US012737951B2

(12) United States Patent
Ote et al.

(10) Patent No.: US 12,737,951 B2
(45) Date of Patent: Sep. 15, 2026

(54) IMAGE PROCESSING DEVICE AND IMAGE PROCESSING METHOD

(71) Applicant: HAMAMATSU PHOTONICS K.K., Hamamatsu (JP)

(72) Inventors: Kibo Ote, Hamamatsu (JP); Fumio Hashimoto, Hamamatsu (JP); Yuya Onishi, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 215 days.

(21) Appl. No.: 18/833,003

(22) PCT Filed: Jan. 30, 2023

(86) PCT No.: PCT/JP2023/002910
§ 371 (c)(1),
(2) Date: Jul. 25, 2024

(87) PCT Pub. No.: WO2023/149403
PCT Pub. Date: Aug. 10, 2023

(65) Prior Publication Data

US 2025/0157099 A1 May 15, 2025

(30) Foreign Application Priority Data

Feb. 2, 2022 (JP) ................................. 2022-014768

(51) Int. Cl.
*G06T 12/00* (2026.01)
*G06T 12/20* (2026.01)
*A61B 6/03* (2006.01)

(52) U.S. Cl.
CPC .............. *G06T 12/20* (2026.01); *A61B 6/037* (2013.01); *G06T 2211/424* (2013.01); *G06T 2211/441* (2023.08)

(58) Field of Classification Search
CPC ............... G06T 12/20; G06T 2211/424; G06T 2211/441; A61B 6/037; A61B 6/032; A61B 6/5205; A61B 6/5258; G01T 1/2985
See application file for complete search history.

(56) References Cited

U.S. PATENT DOCUMENTS

2007/0201611 A1* 8/2007 Pratx ........................ G06T 12/10 378/4
2019/0104940 A1* 4/2019 Zhou .................... A61B 5/0035
(Continued)

FOREIGN PATENT DOCUMENTS

JP 2020-036877 A 3/2020
JP 2020-128882 A 8/2020
(Continued)

OTHER PUBLICATIONS

Gong, Kuang et al., "Iterative PET Image Reconstruction Using Convolutional Neural Network Representation," IEEE Transactions on Medical Imaging, vol. 38, No. 3, https://ieeexplore.ieee.org/abstract/document/8463596, Sep. 12, 2018, pp. 675-685 (Year: 2018).*

(Continued)

*Primary Examiner* — Van D Huynh
(74) *Attorney, Agent, or Firm* — Faegre Drinker Biddle & Reath LLP

(57) ABSTRACT

An image processing method, starting from a certain initial state, creates a tomographic image of a subject by repeatedly performing a reconstruction step, a CNN processing step, and an update step a plurality of times. In the reconstruction step, a first image is created by performing processing by using a list mode iterative reconstruction method. In the CNN processing step, input information is input to a CNN and a second image is created by the CNN by using a DIP technique, and the CNN is trained. In the update step, a third image is updated based on the first image and the second image.

22 Claims, 14 Drawing Sheets

(56) References Cited

U.S. PATENT DOCUMENTS

| | | | | |
|---|---|---|---|---|
| 2019/0325619 | A1* | 10/2019 | Zhang | G06T 12/20 |
| 2020/0043204 | A1* | 2/2020 | Fu | G06T 12/20 |
| 2020/0311871 | A1* | 10/2020 | Yu | G06T 5/50 |
| 2020/0311878 | A1* | 10/2020 | Matsuura | G06T 5/70 |
| 2020/0402644 | A1* | 12/2020 | Zhou | G06T 5/70 |
| 2021/0035339 | A1* | 2/2021 | Ahn | G06N 3/084 |
| 2021/0074036 | A1 | 3/2021 | Fuchs et al. | |
| 2022/0110600 | A1* | 4/2022 | Chan | A61B 6/5258 |
| 2022/0164934 | A1* | 5/2022 | Gao | G06N 3/09 |
| 2024/0185485 | A1* | 6/2024 | Salomon | G06T 12/20 |

FOREIGN PATENT DOCUMENTS

| | | | |
|---|---|---|---|
| JP | 2021-018109 | A | 2/2021 |
| JP | 2021-117866 | A | 8/2021 |
| WO | WO-2020/201755 | A1 | 10/2020 |

OTHER PUBLICATIONS

Reader, A. J. et al., “One-Pass List-Mode EM Algorithm for High-Resolution 3-D PET Image Reconstruction Into Large Arrays,” IEEE Transactions on Nuclear Science, vol. 49, No. 3, 2002, pp. 693-699 (Year: 2002).*

Gong, Kuang et al., “PET Image Reconstruction Using Deep Image Prior,” IEEE Transactions on Medical Imaging, Dec. 2018.

Gong, Kuang et al., “Iterative PET Image Reconstruction Using Convolutional Neural Network Representation,” IEEE Transactions on Medical Imaging, vol. 38, No. 3, https://ieeexplore.ieee.org/abstract/document/8463596, Sep. 12, 2018, pp. 675-685.

Reader, A. J. et al., “One-Pass List-Mode EM Algorithm for High-Resolution 3-D PET Image Reconstruction Into Large Arrays,” IEEE Transactions on Nuclear Science, vol. 49, No. 3, 2002, pp. 693-699.

International Preliminary Report on Patentability mailed Aug. 15, 2024 for PCT/JP2023/002910.

* cited by examiner

LIST DATA
INPUT INFORMATION z
RECONSTRUCTION
CNN PROCESSING
UPDATE
S1(1)
S2(1)
S3(1)
S1(n-1)
S2(n-1)
S3(n-1)
S1(n)
S2(n)
S3(n)
S1(N)
S2(N)
S3(N)
$x^{(n-1)}$
$f_\theta^{(n-1)}$
$\mu^{(n-1)}$
$x^{(n)}$
$f_\theta^{(n)}$
$\mu^{(n)}$ (a)

(b)

(a)

(b)

(a)

(b)

(a)

(b)

(a)

(b)

(a)

(b)

(a)

(b)

(a)

(b)

LIST DATA
INPUT INFORMATION z
S1(1)
RECONSTRUCTION
S3(1)
UPDATE
S2(1)
CNN PROCESSING
S1(n-1)
RECONSTRUCTION
$x_{ML}^{(n-1)}$
S3(n-1)
UPDATE
$f_\theta^{(n-1)}$
S2(n-1)
CNN PROCESSING
$x^{(n-1)}$
S1(n)
RECONSTRUCTION
$x_{ML}^{(n)}$
S3(n)
UPDATE
$f_\theta^{(n)}$
S2(n)
CNN PROCESSING
$x^{(n)}$
S1(N)
RECONSTRUCTION
S3(N)
UPDATE
S2(N)
CNN PROCESSING

IMAGE PROCESSING DEVICE AND IMAGE PROCESSING METHOD

TECHNICAL FIELD

The present disclosure relates to an apparatus and a method for creating a tomographic image based on list data collected by a radiation tomography apparatus.

BACKGROUND ART

Radiation tomography apparatuses capable of acquiring a tomographic image of a subject (living body) include a positron emission tomography (PET) apparatus and a single photon emission computed tomography (SPECT) apparatus.

The PET apparatus includes a detection unit having a large number of small radiation detectors arranged around a measurement space in which the subject is placed. The PET apparatus detects a photon pair of an energy of 511 keV generated by electron positron annihilation in the subject into which a positron-emitting isotope (RI source) is introduced by a coincidence method using the detection unit, and collects coincidence information thereof. Then, a tomographic image representing a spatial distribution of generation frequency of the photon pairs in the measurement space (that is, a spatial distribution of the RI sources) can be reconstructed based on the collected many pieces of coincidence information described above.

In this case, a dynamic PET image including the tomographic images of a plurality of frames can be obtained by dividing list data in which the coincidence information collected by the PET apparatus is arranged in time series into the plurality of frames in a collection order, and performing image reconstruction processing using a data group included in each frame out of the list data. The PET apparatus plays an important role in a nuclear medicine field and the like, and can be used to study, for example, a biological function or a brain high-order function.

The tomographic image which is reconstructed as described above contains a lot of noise, and therefore, noise removal processing by an image filter is necessary. Examples of the image filter used for performing the noise removal include a Gaussian filter and a guided filter. Conventionally, the Gaussian filter is used. On the other hand, the guided filter is developed in recent years, and further, has a feature of being able to preserve a boundary of shading in the image compared with the Gaussian filter.

Further, a technique for removing noise in the tomographic image by a deep image prior technique using a convolutional neural network, which is a type of a deep neural network, has been proposed (Non Patent Document 1). Hereinafter, the deep neural network is referred to as a "DNN", the convolutional neural network is referred to as a "CNN", and the deep image prior technique is referred to as a "DIP technique".

In the DIP technique, the noise in the object image can be reduced by using a property of the CNN that a meaningful structure in the object image is learned faster than random noise (that is, the random noise is less likely to be learned).

In each of the noise removal techniques described above, the tomographic image is created by a histogram mode reconstruction method by using the list data, and then the tomographic image is processed to reduce the noise. In addition, in some cases, the noise removal technique may be incorporated into the histogram mode reconstruction method as regularization.

In the histogram mode reconstruction method, a histogram representing the number of coincidence events detected by each detector pair is created based on the list data, and the tomographic image is reconstructed based on the above histogram. As a format of the histogram, for example, a four-dimensional array (three-dimensional sinogram) of radius×body axis×azimuth×inclination angle is used.

In addition, with the evolution of the radiation tomography technique in recent years, in the case in which new information such as detection time difference information (time of flight, TOF) of a pair of radiation detectors, a photon interaction depth (depth of interaction, DOI) in the detector and the like is added to the list data, an array of the format of the histogram becomes a high dimension such as five dimensions or six dimensions. As a result, in the histogram mode reconstruction method in which the tomographic image is reconstructed from the list data through the histogram, the load of an operation unit including a CPU and the like for performing a series of the above processes becomes excessive.

A list mode iterative reconstruction method has been proposed as a technique capable of addressing the problem of the histogram mode reconstruction method described above (Non Patent Document 2). In the list mode iterative reconstruction method, the tomographic image is reconstructed by repeatedly performing iterative approximation directly from the list data (without passing through the histogram).

CITATION LIST

Non Patent Literature

Non Patent Document 1: Kuang Gong et al., "PET Image Reconstruction Using Deep Image Prior", IEEE Transactions on Medical Imaging, December 2018

Non Patent Document 2: A. J. Reader et al., "One-Pass List-Mode EM Algorithm for High-Resolution 3-D PET Image Reconstruction Into Large Arrays", IEEE Transactions on Nuclear Science, Vol. 49, No. 3, pp. 693-699, 2002

SUMMARY OF INVENTION

Technical Problem

Many noise removal techniques have been researched and developed for the histogram mode reconstruction method. However, the list mode iterative reconstruction method has a problem in that it is difficult to directly process the list data by using the CNN, and thus, a technique for the list mode iterative reconstruction method capable of effectively removing the noise by incorporating the CNN is not known.

An object of the present invention is to provide an image processing apparatus and an image processing method capable of creating a tomographic image in which noise is reduced based on list data collected by a radiation tomography apparatus.

Solution to Problem

A first aspect of the present invention is an image processing apparatus. The image processing apparatus is an image processing apparatus for creating a tomographic image based on list data collected by a radiation tomography apparatus, and includes (1) a reconstruction unit for newly creating a first image by repeatedly performing processing of bringing an image obtained by updating the first image based on the list data by using a list mode iterative reconstruction method close to a difference between a second image and a third image; (2) a CNN processing unit for inputting input information to a convolutional neural network, creating the second image by the convolutional neural network, and training the convolutional neural network so as to bring the created second image close to a sum of the first image and the third image; and (3) an update unit for updating the third image based on the first image and the second image, and starting from an initial state of each of a training state of the convolutional neural network, the first image, the second image, and the third image, creation of the first image by the reconstruction unit, creation of the second image and training of the convolutional neural network by the CNN processing unit, and update of the third image by the update unit are repeatedly performed, and any one of the first image and the second image obtained by repeated processing is set as the tomographic image.

A second aspect of the present invention is an image processing apparatus. The image processing apparatus is an image processing apparatus for creating a tomographic image based on list data collected by a radiation tomography apparatus, and includes (1) a reconstruction unit for creating a first image by updating a third image based on the list data by using a list mode iterative reconstruction method; (2) a CNN processing unit for inputting input information to a convolutional neural network, creating a second image by the convolutional neural network, and training the convolutional neural network so as to bring the created second image close to the third image; and (3) an update unit for updating the third image based on the first image and the second image, and starting from an initial state of each of a training state of the convolutional neural network and the third image, creation of the first image by the reconstruction unit, creation of the second image and training of the convolutional neural network by the CNN processing unit, and update of the third image by the update unit are repeatedly performed, and any one of the first image, the second image, and the third image obtained by repeated processing is set as the tomographic image.

An embodiment of the present invention is a radiation tomography system. The radiation tomography system includes a radiation tomography apparatus for collecting list data for reconstructing a tomographic image of a subject; and the image processing apparatus of the above configuration for creating the tomographic image based on the list data collected by the radiation tomography apparatus.

A first aspect of the present invention is an image processing method. The image processing method is an image processing method for creating a tomographic image based on list data collected by a radiation tomography apparatus, and includes (1) a reconstruction step of newly creating a first image by repeatedly performing processing of bringing an image obtained by updating the first image based on the list data by using a list mode iterative reconstruction method close to a difference between a second image and a third image; (2) a CNN processing step of inputting input information to a convolutional neural network, creating the second image by the convolutional neural network, and training the convolutional neural network so as to bring the created second image close to a sum of the first image and the third image; and (3) an update step of updating the third image based on the first image and the second image, and starting from an initial state of each of a training state of the convolutional neural network, the first image, the second image, and the third image, creation of the first image in the reconstruction step, creation of the second image and training of the convolutional neural network in the CNN processing step, and update of the third image in the update step are repeatedly performed, and any one of the first image and the second image obtained by repeated processing is set as the tomographic image.

A second aspect of the present invention is an image processing method. The image processing method is an image processing method for creating a tomographic image based on list data collected by a radiation tomography apparatus, and includes (1) a reconstruction step of creating a first image by updating a third image based on the list data by using a list mode iterative reconstruction method; (2) a CNN processing step of inputting input information to a convolutional neural network, creating a second image by the convolutional neural network, and training the convolutional neural network so as to bring the created second image close to the third image; and (3) an update step of updating the third image based on the first image and the second image, and starting from an initial state of each of a training state of the convolutional neural network and the third image, creation of the first image in the reconstruction step, creation of the second image and training of the convolutional neural network in the CNN processing step, and update of the third image in the update step are repeatedly performed, and any one of the first image, the second image, and the third image obtained by repeated processing is set as the tomographic image.

Advantageous Effects of Invention

According to the aspects of the present invention, a tomographic image in which noise is reduced can be created based on list data collected by a radiation tomography apparatus.

DESCRIPTION OF EMBODIMENTS

Hereinafter, embodiments of an image processing apparatus and an image processing method will be described in detail with reference to the accompanying drawings. In the description of the drawings, the same elements will be denoted by the same reference signs, and redundant description will be omitted. The present invention is not limited to these examples.

Figure 1:
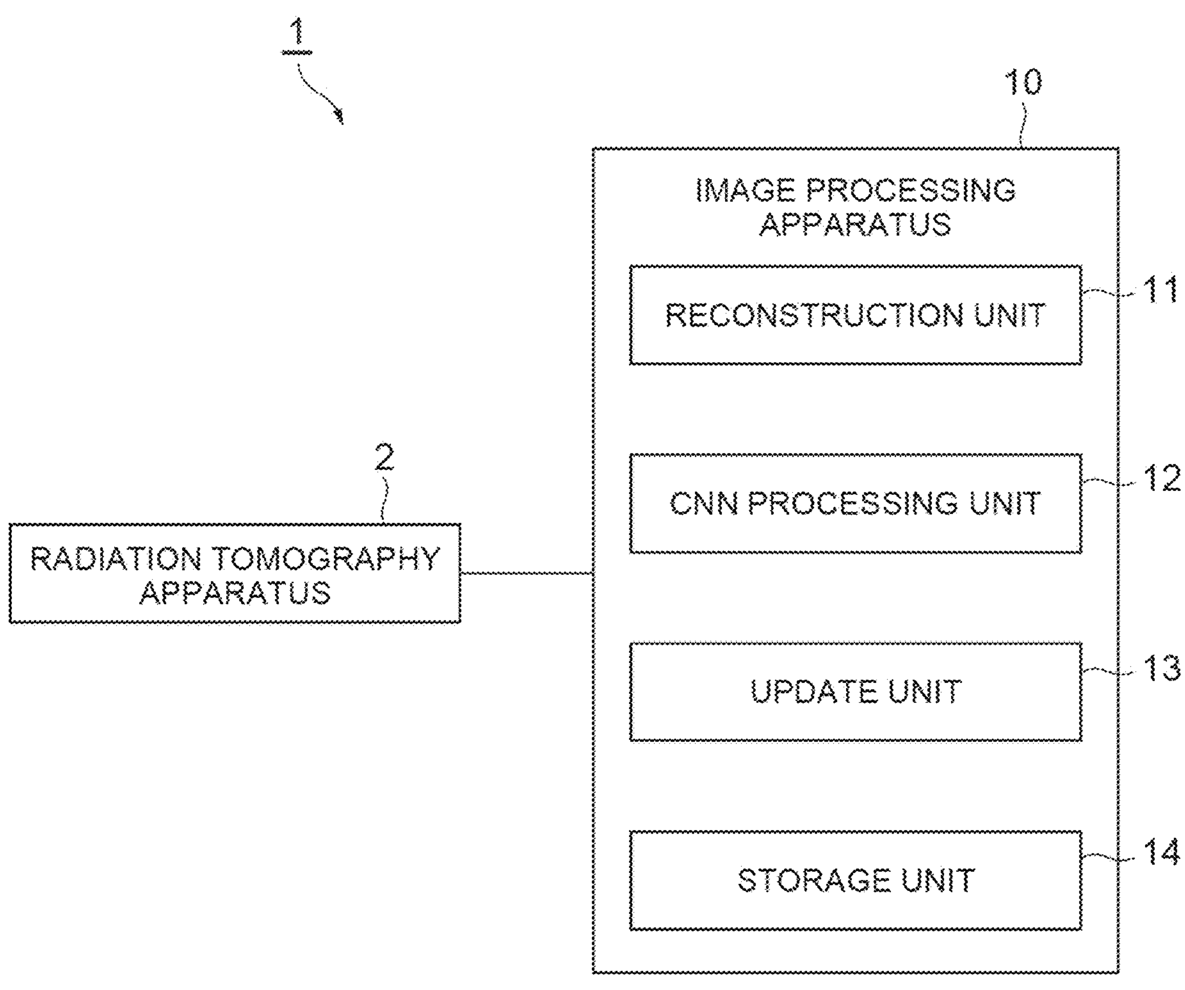
FIG. 1 is a diagram illustrating a configuration of a radiation tomography system 1.

FIG. 1 is a diagram illustrating a configuration of a radiation tomography system 1. The radiation tomography system 1 includes a radiation tomography apparatus 2 and an image processing apparatus 10. The image processing apparatus 10 includes a reconstruction unit 11, a CNN processing unit 12, an update unit 13, and a storage unit 14.

As the image processing apparatus 10, a computer including a CPU, a RAM, a ROM, a hard disk drive, and the like is used. Further, the image processing apparatus 10 includes an input unit (for example, a keyboard or a mouse) for receiving an input of an operator, and further, includes a display unit (for example, a liquid crystal display) for displaying an image and the like.

The radiation tomography apparatus 2 is an apparatus for collecting list data for reconstructing a tomographic image of a subject. Examples of the radiation tomography apparatus 2 include a PET apparatus and a SPECT apparatus. In the following description, it is assumed that the radiation tomography apparatus 2 is the PET apparatus.

The radiation tomography apparatus 2 includes a detection unit having a large number of small radiation detectors being arranged around a measurement space in which the subject is placed. The radiation tomography apparatus 2 detects a photon pair of an energy of 511 keV generated by electron positron annihilation in the subject into which a positron-emitting isotope (RI source) is injected by a coincidence method using the detection unit, and accumulates coincidence information thereof. In addition, the radiation tomography apparatus 2 outputs, to the image processing apparatus 10, the list data in which the accumulated many pieces of the coincidence information are arranged in time series.

The list data includes identification information and detection time information of a pair of radiation detectors used in the coincidence detection of the photon pair. The list data may further include detection time difference information (TOF information) of the pair of radiation detectors, photon interaction depth information (DOI information) in the radiation detector, energy information of the photons detected by the radiation detectors, and the like.

The storage unit 14 stores the list data collected by the radiation tomography apparatus 2. Further, the storage unit 14 also stores a program for causing the reconstruction unit 11, the CNN processing unit 12, and the update unit 13 to execute respective steps of processing. The reconstruction unit 11, the CNN processing unit 12, and the update unit 13 create the tomographic image of the subject using the program and the list data stored by the storage unit 14.

The reconstruction unit 11 performs processing based on the list mode iterative reconstruction method (see Non Patent Document 2) to create a first image. In the processing based on the list mode iterative approximation reconstruction method performed in the reconstruction unit 11, an iterative update formula such as an LM-MLEM (maximum likelihood expectation maximization), an LM-OSEM (ordered subset EM), an LM-DRAMA (dynamic row action maximum likelihood algorithm), or the like is used.

The CNN processing unit 12 performs processing based on the DIP technique (see Non Patent Document 1) to create a second image. In the processing based on the DIP technique performed in the CNN processing unit 12, input information is input to a CNN, the second image is created by the CNN, and further, the CNN is trained. The input information to be input to the CNN may be form information of the subject, may be an MRI image or a CT image of the subject, or may be a random noise image.

The update unit 13 updates a third image based on the first image and the second image. The details of the respective processes performed by the reconstruction unit 11, the CNN processing unit 12, and the update unit 13 will be described later.

The storage unit 14 also stores the input information to be input to the CNN, and further, also stores the first image, the second image, and the third image. In the image processing apparatus 10, starting from a certain initial state, the respective processes of the reconstruction unit 11, the CNN processing unit 12, and the update unit 13 are repeatedly performed, and the tomographic image of the subject is created.

Figure 2:
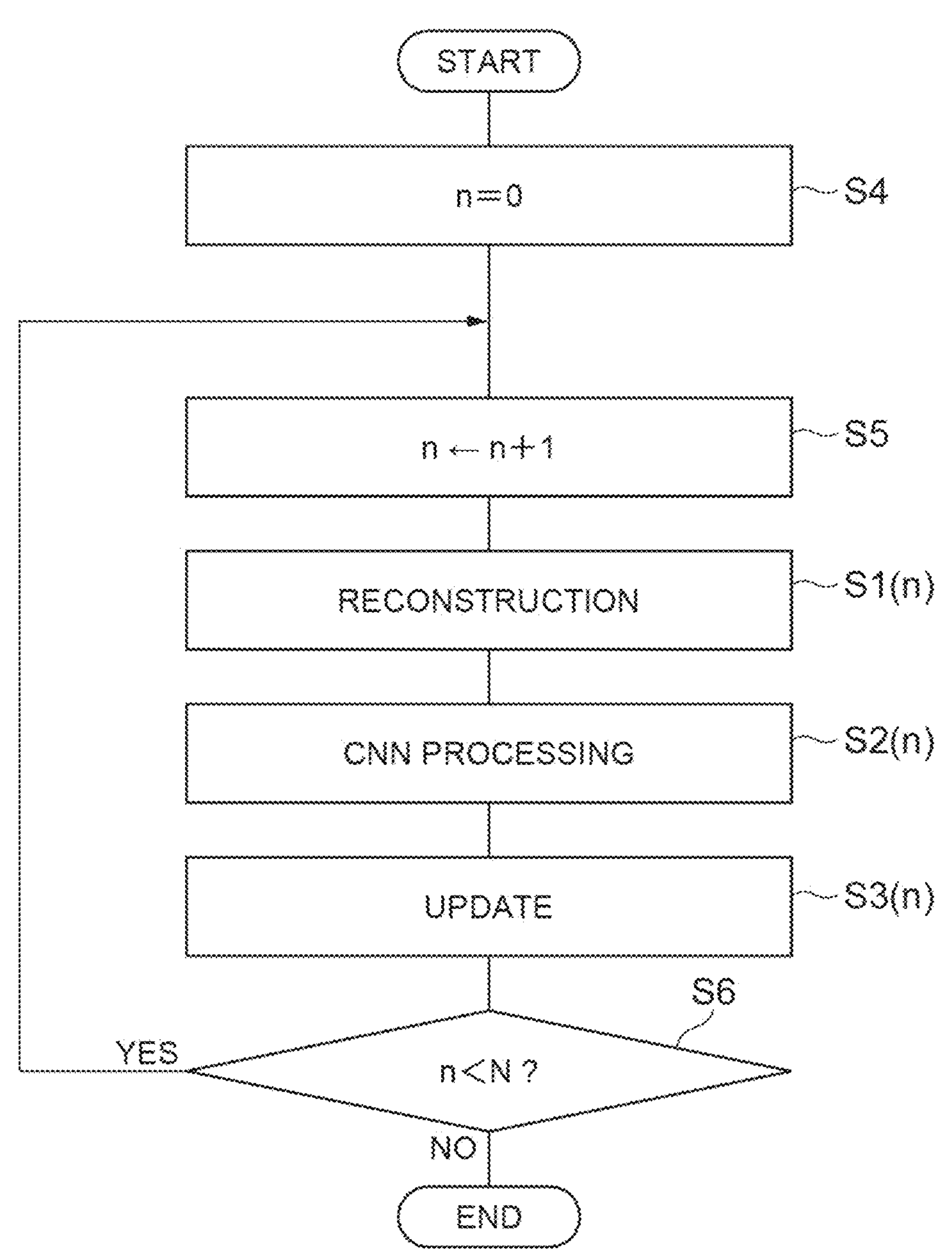
FIG. 2 is a flowchart illustrating an image processing method.

FIG. 2 is a flowchart illustrating an image processing method. The image processing method includes a reconstruction step S1 performed by the reconstruction unit 11, a CNN processing step S2 performed by the CNN processing unit 12, and an update step S3 performed by the update unit 13. Starting from the certain initial state, the reconstruction step S1, the CNN processing step S2, and the update step S3 are repeatedly performed a plurality of times (N times) to create the tomographic image of the subject.

In a step S4, a value of a parameter n is set to an initial value of 0. In a subsequent step S5, the value of the parameter n is increased by 1. After the step S5, the reconstruction step S1, the CNN processing step S2, and the update step S3 are performed. In a step S6 subsequent to these steps, the value of the parameter n is compared with N, and in the case in which it is determined that n is smaller than N, the process returns to the step S5. In the case in which, in the step S6, it is determined that n has reached N, the repeated processing is to be ended, and the tomographic image of the subject is acquired.

In the following description, out of the N times of the steps of the repeated processing, an n-th reconstruction step S1 is referred to as a reconstruction step S1(*n*), an n-th CNN processing step S2 is referred to as a CNN processing step S2(*n*), and an n-th update step S3 is referred to as an update step S3(*n*). n is an integer of 1 or more and N or less.

Next, the details of the processing of the image processing apparatus 10 and the image processing method will be described. First, the list data U is formulated as in the following Formula (1). t is a number indicating the coincidence event. T is the total number of the events. i(t) indicates a number for identifying a detector pair used in the detection of the t-th event.

[Formula 1]

$$U = \{i(t) \mid t = 1, 2, \ldots, T\} \tag{1}$$

For the above list data U, a constrained optimization problem represented by the following Formula (2) is considered. x is the tomographic image. L(U|x) is a likelihood indicating a probability that the list data U is observed from the tomographic image x. z is the input information to be input to the CNN. θ is a parameter indicating a training state of the CNN, such as a connection weight and the like, and changes as the training of the CNN progresses. $f_\theta(z)$ is an image output from the CNN in the case in which the input information z is input to the CNN with the training state of θ. The constrained optimization problem of the above Formula (2) is a problem of optimizing the tomographic image x and the CNN parameter θ such that the likelihood L(U|x) becomes high, under the constraint ($x=f_\theta(z)$) that the tomographic image x becomes the CNN output image $f_\theta(z)$.

[Formula 2]

$$\begin{aligned} &\max L(U \mid x) \\ &\text{s.t. } x = f_\theta(z) \end{aligned} \tag{2}$$

As an aspect of a solution method of the optimization problem described above, there are a first aspect and a second aspect as described below. The first aspect includes processing based on an alternating direction method of multipliers (ADMM method). The second aspect includes processing based on a forward backward splitting (FBS method). In addition, in the FBS method, a De Pierro method as a special aspect of the FBS method is also included. In the following description, the details of the image processing method of each of the first aspect and the second aspect will be described.

In the image processing method of the first aspect, the constrained optimization problem of the above Formula (2) is rewritten based on an augmented Lagrangian function method, and then solved by using the ADMM method. In the augmented Lagrangian function method, the constraint in the above Formula (2) is replaced by a regularization term, and the constrained optimization problem represented by the above Formula (2) is rewritten as an unconstrained optimization problem represented by the following Formula (3). ρ is a positive constant for adjusting a strength of the regularization. μ is a parameter called a Lagrange multiplier or a dual variable, and is referred to as the "third image" in the following description.

[Formula 3]

$$\min - L(U \mid x) + \frac{\rho}{2}\|x - f_\theta(z) + \mu\|^2 + \frac{\rho}{2}\|\mu\|^2 \tag{3}$$

In the first aspect, by the ADMM, the unconstrained optimization problem of the above Formula (3) is solved by repeatedly performing processes of the following Formula (4) to Formula (6).

[Formula 4]

$$x^{(n)} = \underset{x}{\operatorname{argmax}} L(U \mid x) \to \frac{\rho}{2}\left\|x - f_{\theta^{(n-1)}}(z) + \mu^{(n-1)}\right\|^2 \tag{4}$$

[Formula 5]

$$\theta^{(n)} = \underset{\theta}{\operatorname{argmin}}\left\|f_\theta(z) - x^{(n)} - \mu^{(n-1)}\right\|^2 \tag{5}$$

[Formula 6]

$$\mu^{(n)} = \mu^{(n-1)} + x^{(n)} - f_{\theta^{(n)}}(z) \tag{6}$$

Figure 3:
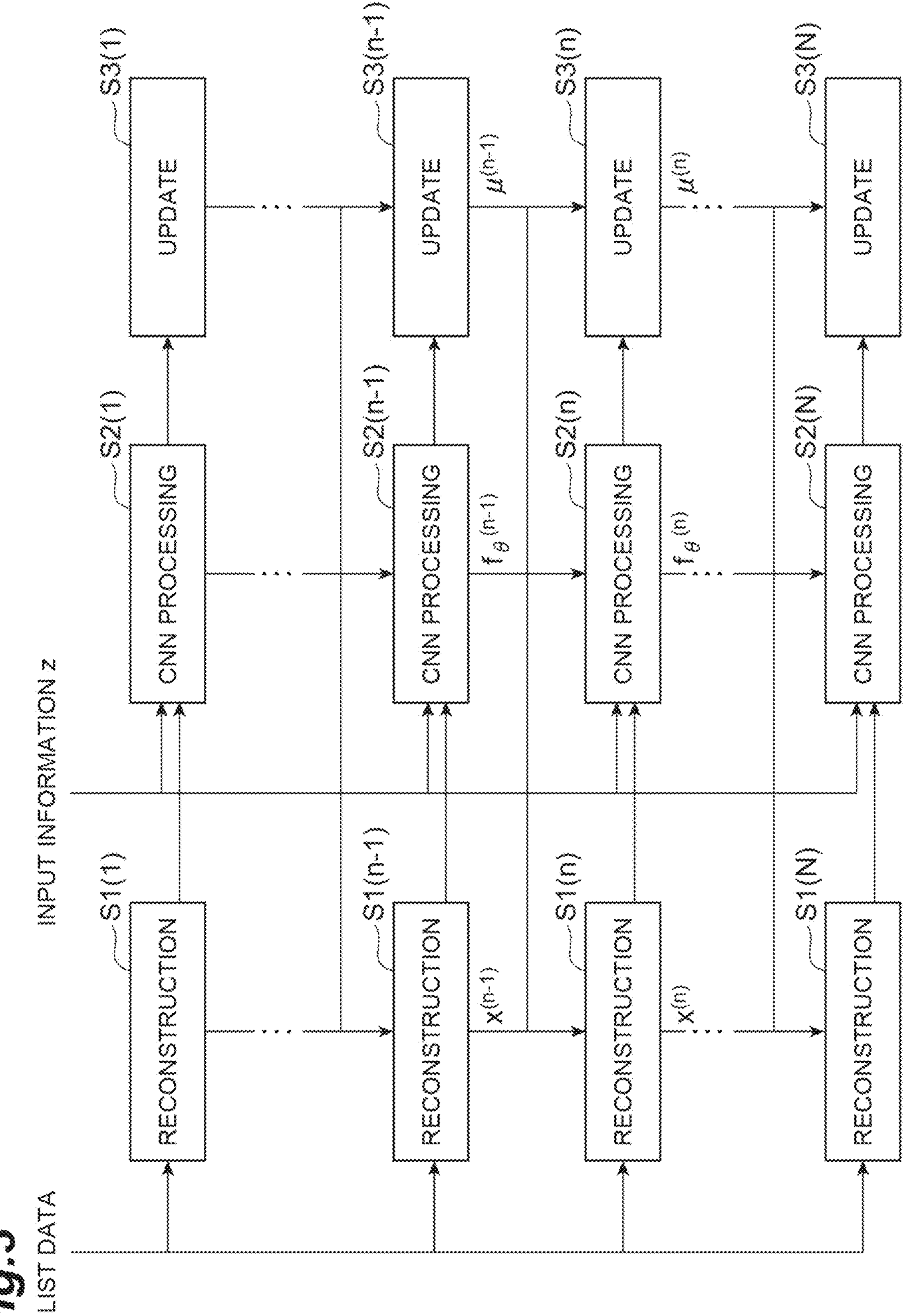
FIG. 3 is a diagram illustrating a sequence of the image processing method according to a first aspect.

FIG. 3 is a diagram illustrating a sequence of the image processing method according to the first aspect. Prior to performing the repeated processing, the training state $\theta^{(0)}$ of the CNN, the first image $x^{(0)}$, the second image $$f_\theta^{(0)}(z),$$

and the third image $\mu^{(0)}$ are respectively initialized. In addition, the second image $$f_\theta^{(0)}(z)$$

is an image output from the CNN in the case in which the input information z is input to the CNN with the initial training state of $\theta^{(0)}$.

In the n-th reconstruction step S1(*n*), according to the above Formula (4), the first image $x^{(n)}$ is newly created by repeatedly performing the processing of bringing an image obtained by performing the update of the first image $x^{(n-1)}$ once based on the list data U by using the list mode iterative reconstruction method close to a difference $$\left(f_\theta^{(n-1)}(z) - \mu^{(n-1)}\right)$$

between the second image $$f_\theta^{(n-1)}(z)$$

and the third image $\mu^{(n-1)}$.

In the n-th CNN processing step S2(*n*), according to the above Formula (5), the input information z is input to the CNN, and the second image $$f_\theta^{(n)}(z)$$

is created by the CNN, and further, the CNN is trained so as to bring the created second image $$f_{\theta}^{(n)}(z)$$

close to a sum $(x^{(n)}+\mu^{(n-1)})$ of the first image $x^{(n)}$ and the third image $\mu^{(n-1)}$. The training state of the CNN after the above training is set to $\theta^{(n)}$.

In the n-th update step S3(*n*), according to the above Formula (6), a difference $$\left(x^{(n)} - f_{\theta}^{(n)}(z)\right)$$

between the first image $x^{(n)}$ and the second image $$f_{\theta}^{(n)}(z)$$

is added to the third image $\mu^{(n-1)}$, and thus, it is updated to the third image $\mu^{(n)}$.

When the N times of the steps of the repeated processing of the reconstruction step S1, the CNN processing step S2, and the update step S3 are completed, any one of the first image $x^{(N)}$ and the second image $$f_{\theta}^{(N)}(z)$$

obtained as a result of the repeated processing is set as the tomographic image of the subject.

In the first aspect, the first image x and the second image $f_{\theta}(z)$ are not optimized at the same time, but the first image x and the second image $f_{\theta}(z)$ are optimized alternately, and thus, it is easy to solve the problem. Further, the processing of the reconstruction step S1 performed by the reconstruction unit 11 and the processing of the CNN processing step S2 performed by the CNN processing unit 12 can be performed by the conventional techniques as described in, for example, Non Patent Documents 1 and 2, and thus, it is easy to implement.

FIG. 4 to FIG. 11 are diagrams showing results of a simulation performed for confirming the effect of the image processing method according to the first aspect. In the present simulation, simulation data was created by an MC simulation of a head PET apparatus using a digital brain phantom image, and the effect of the image processing method of the first aspect was confirmed by using the created simulation data.

Figure 4:
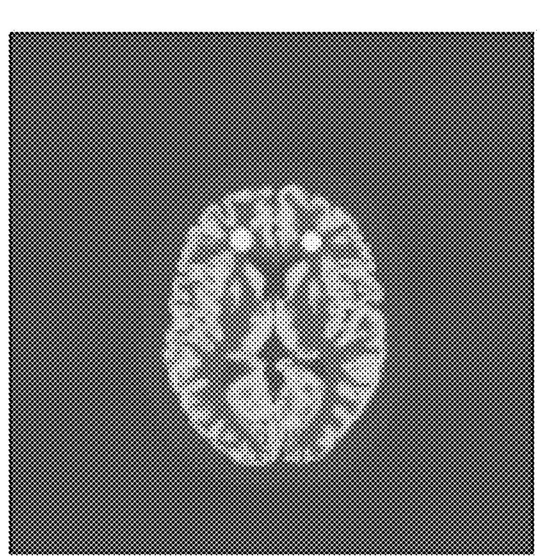
FIG. 4 includes diagrams each showing a phantom image (correct image), and shows (a) an image of a transverse section, and (b) an image of the transverse section.
Figure 4:
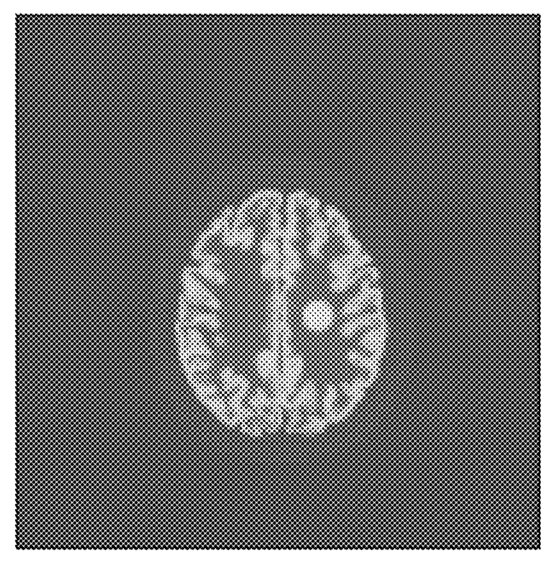
Figure 5:
FIG. 5 includes diagrams each showing the phantom image (correct image), and shows (a) an image of a coronal section, and (b) an image of a sagittal section.
Figure 5:
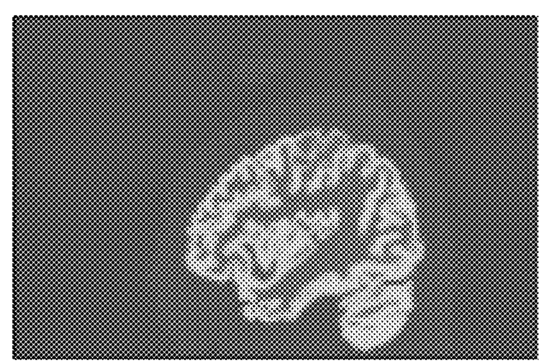

FIG. 4 and FIG. 5 include diagrams each showing a phantom image (correct image). Each of (a) in FIG. 4 and (b) in FIG. 4 shows an image of the transverse section, (a) in FIG. 5 shows an image of the coronal section, and (b) in FIG. 5 shows an image of the sagittal section.

Figure 6:
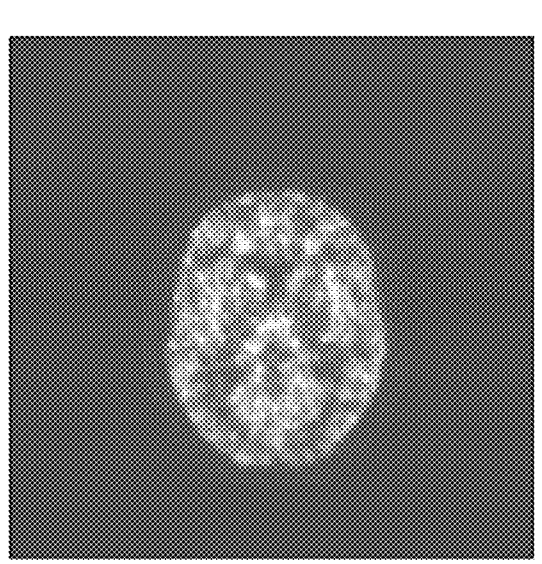
FIG. 6 includes diagrams each showing a tomographic image obtained by the image processing method according to a first comparative example, and shows (a) an image of the transverse section, and (b) an image of the transverse section.
Figure 6:
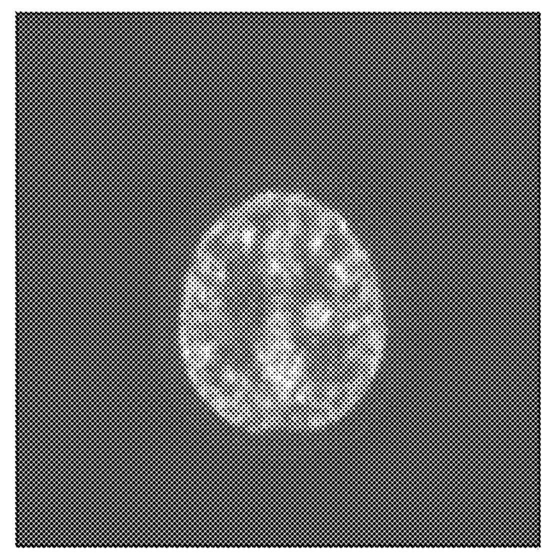
Figure 7:
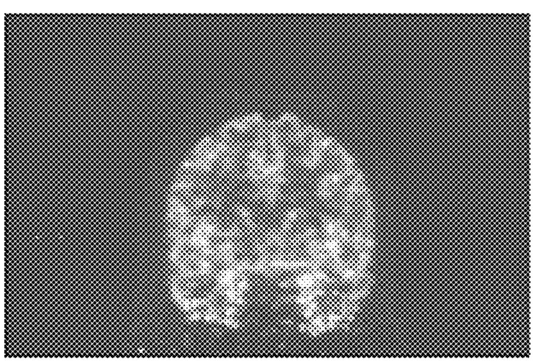
FIG. 7 includes diagrams each showing the tomographic image obtained by the image processing method according to the first comparative example, and shows (a) an image of the coronal section, and (b) an image of the sagittal section.
Figure 7:
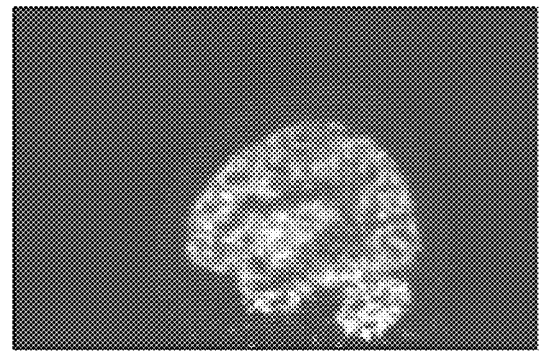

FIG. 6 and FIG. 7 include diagrams each showing the tomographic image obtained by the image processing method according to a first comparative example. Each of (a) in FIG. 6 and (b) in FIG. 6 shows an image of the transverse section, (a) in FIG. 7 shows an image of the coronal section, and (b) in FIG. 7 shows an image of the sagittal section. The tomographic image of the first comparative example is obtained by reconstructing using only the iterative update formula of the LM-DRAMA of the list mode iterative reconstruction method, and the noise reduction processing is not performed.

Figure 8:
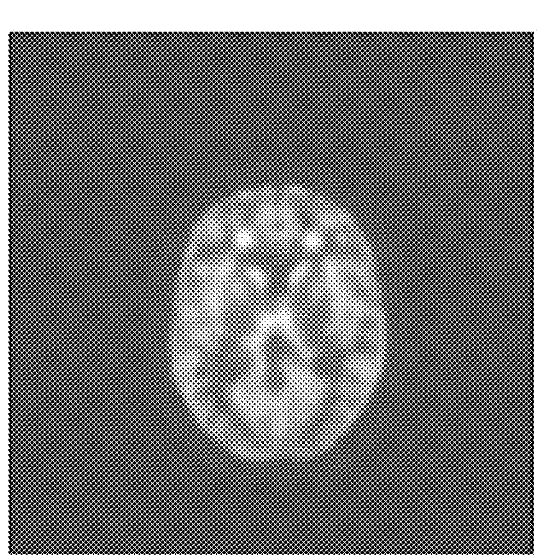
FIG. 8 includes diagrams each showing the tomographic image obtained by the image processing method according to a second comparative example, and shows (a) an image of the transverse section, and (b) an image of the transverse section.
Figure 8:
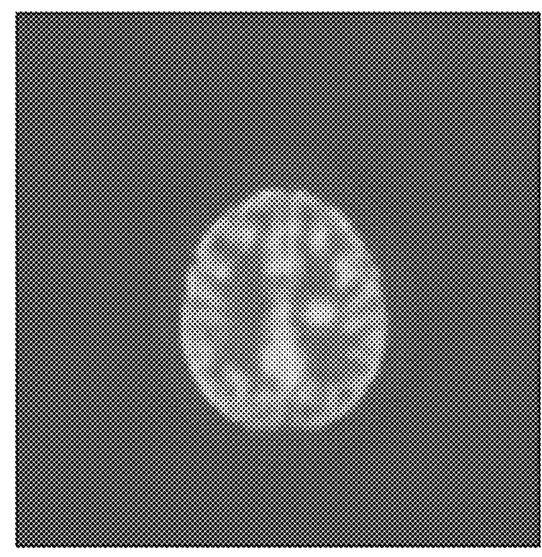
Figure 9:
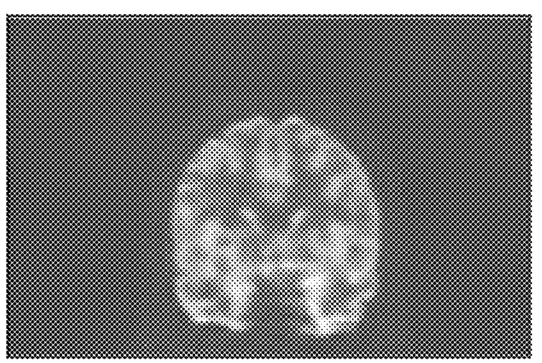
FIG. 9 includes diagrams each showing the tomographic image obtained by the image processing method according to the second comparative example, and shows (a) an image of the coronal section, and (b) an image of the sagittal section.
Figure 9:
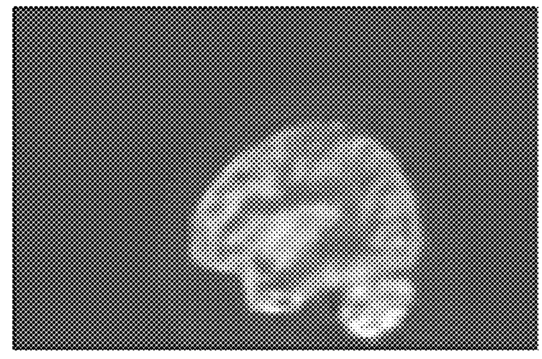

FIG. 8 and FIG. 9 include diagrams each showing the tomographic image obtained by the image processing method according to a second comparative example. Each of (a) in FIG. 8 and (b) in FIG. 8 shows an image of the transverse section, (a) in FIG. 9 shows an image of the coronal section, and (b) in FIG. 9 shows an image of the sagittal section. The tomographic image of the second comparative example is obtained by reducing the noise by the DIP technique for the reconstructed tomographic image of the first comparative example. The number of times of the parameter update of the CNN is set to 20. The input information input to the CNN is set to the MRI image.

Figure 10:
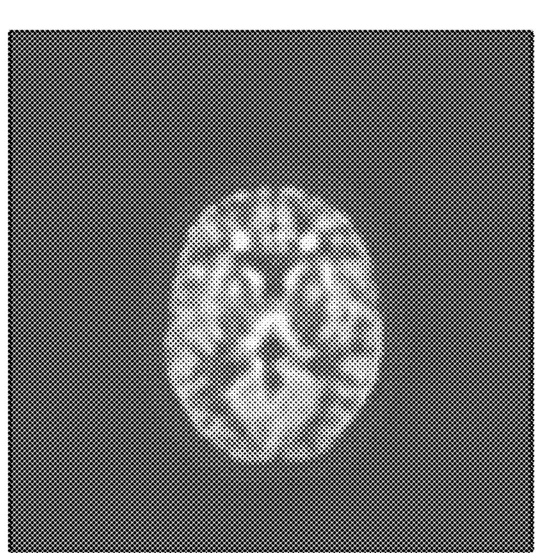
FIG. 10 includes diagrams each showing the tomographic image obtained by the image processing method according to an example, and shows (a) an image of the transverse section, and (b) an image of the transverse section.
Figure 10:
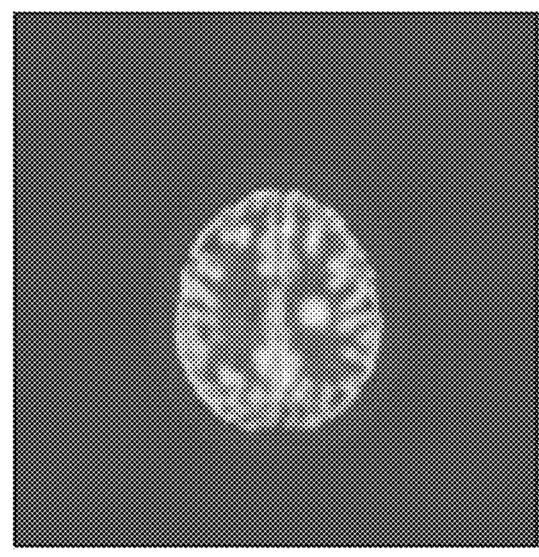
Figure 11:
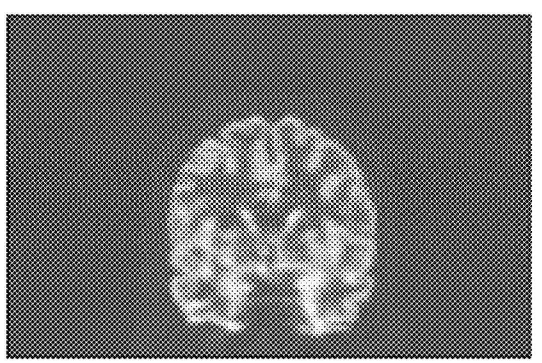
FIG. 11 includes diagrams each showing the tomographic image obtained by the image processing method according to the example, and shows (a) an image of the coronal section, and (b) an image of the sagittal section.
Figure 11:
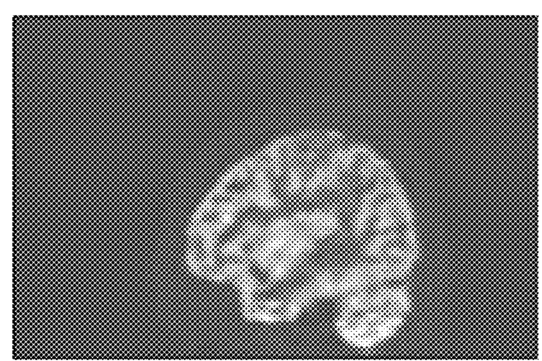

FIG. 10 and FIG. 11 include diagrams each showing the tomographic image obtained by the image processing method according to an example. Each of (a) in FIG. 10 and (b) in FIG. 10 shows an image of the transverse section, (a) in FIG. 11 shows an image of the coronal section, and (b) in FIG. 11 shows an image of the sagittal section. The tomographic image of the example is created by using the image processing method according to the first aspect. It is set to $\rho$=0.05. The input information z input to the CNN is set to the MRI image. The number of repetitions in the reconstruction step S1 is set to 2, the number of repetitions of the training of the CNN in the CNN processing step S2 is set to 20, and the number of repetitions N of the total is set to 200.

As can be seen by comparing the above tomographic images, in the tomographic image obtained by the image processing method according to the example, the noise is reduced, and further, the structure of the cerebral cortex is well reconstructed.

Figure 12:
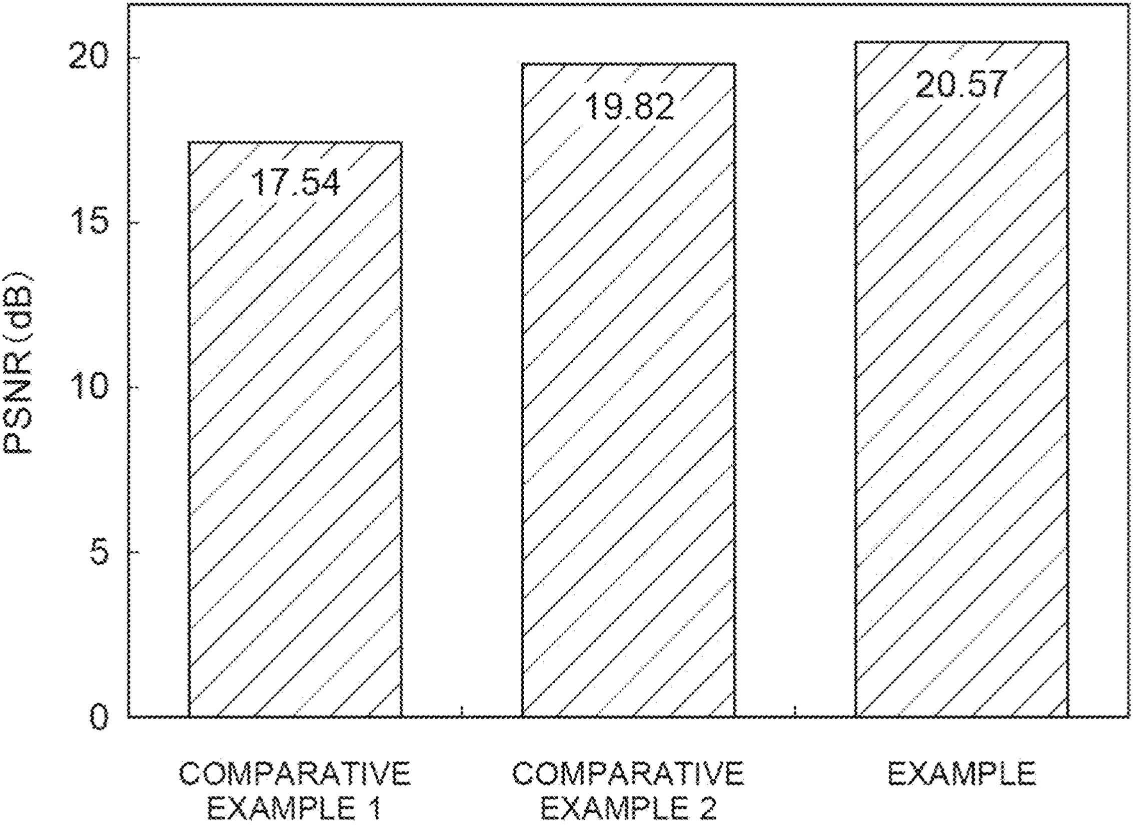
FIG. 12 is a graph showing a PSNR of the tomographic image obtained by each of the first and second comparative examples and the example.
Figure 13:
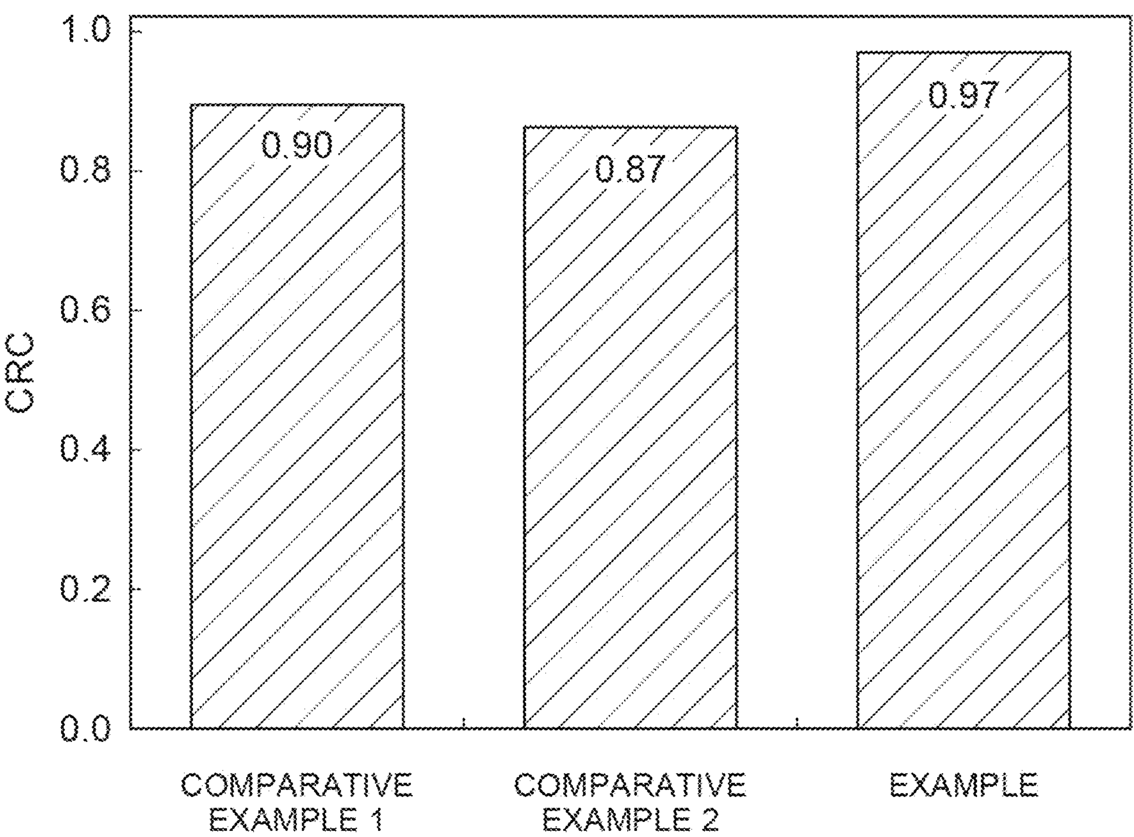
FIG. 13 is a graph showing a CRC of the tomographic image obtained by each of the first and second comparative examples and the example.

FIG. 12 is a graph showing a PSNR of the tomographic image obtained by each of the first and second comparative examples and the example. The PSNR is a peak signal to noise ratio [unit: dB], which is an index of the noise. FIG. 13 is a graph showing a CRC of the tomographic image obtained by each of the first and second comparative examples and the example. The CRC is a contrast recovery coefficient of a tumor, which is an index of the quantitativity.

As compared with the tomographic image of each of the first and second comparative examples, the tomographic image of the example has large values respectively in the PSNR and the CRC, and the CRC is a value close an ideal value of 1.0. As can be seen from the above results, in the image processing method according to the example, it is possible to generate a highly quantitative tomographic image while suppressing an increase in noise artifacts.

Next, the image processing method according to the second aspect will be described. In the image processing method of the second aspect, the constrained optimization problem of the above Formula (2) is solved by the FBS method based on a framework of a maximum a posteriori (MAP) estimation method. In the MAP estimation method, the constrained optimization problem represented by the above Formula (2) is rewritten as an unconstrained optimization problem represented by the following Formula (7).

[Formula 7]

$$\min - L(U \mid x) + \frac{\rho}{2}\|x - f_{\theta}(z)\|^2 \tag{7}$$

In the second aspect, by the FBS, the unconstrained optimization problem of the above Formula (7) is solved by repeatedly performing processes of the following Formula (8) to Formula (11).

[Formula 8]

$$x_{ML}^{(n)} = \underset{x}{\operatorname{argmax}} L(U \mid x) \tag{8}$$

[Formula 9]

$$\theta^{(n)} = \underset{\theta}{\operatorname{argmin}} \| f_\theta(z) - x^{(n-1)} \|^2 \tag{9}$$

[Formula 10]

$$x_{Reg}^{(n)} = x^{(n-1)} + \rho\gamma\left(f_{\theta^{(n)}}(z) - x^{(n-1)}\right) \tag{10}$$

[Formula 11]

$$x^{(n)} = \frac{2x_{ML}^{(n)}}{\left(1 - \frac{1}{\gamma\omega} x_{Reg}^{(n)}\right) + \sqrt{\left(1 - \frac{1}{\gamma\omega} x_{Reg}^{(n)}\right)^2 + 4\frac{1}{\gamma\omega} x_{ML}^{(n)}}} \tag{11}$$

In this case, $\gamma$ is a parameter image provided in advance. $\omega$ is an image representing a sensitivity of the detector for each pixel. When a probability that the $\gamma$-ray pair emitted from the pixel j is detected by the detector pair i is set to $p_{ij}$, the sensitivity image $\omega$ is represented by the following formula (12).

[Formula 12]

$$\omega_j = \sum_i p_{ij} \tag{12}$$

Figure 14:
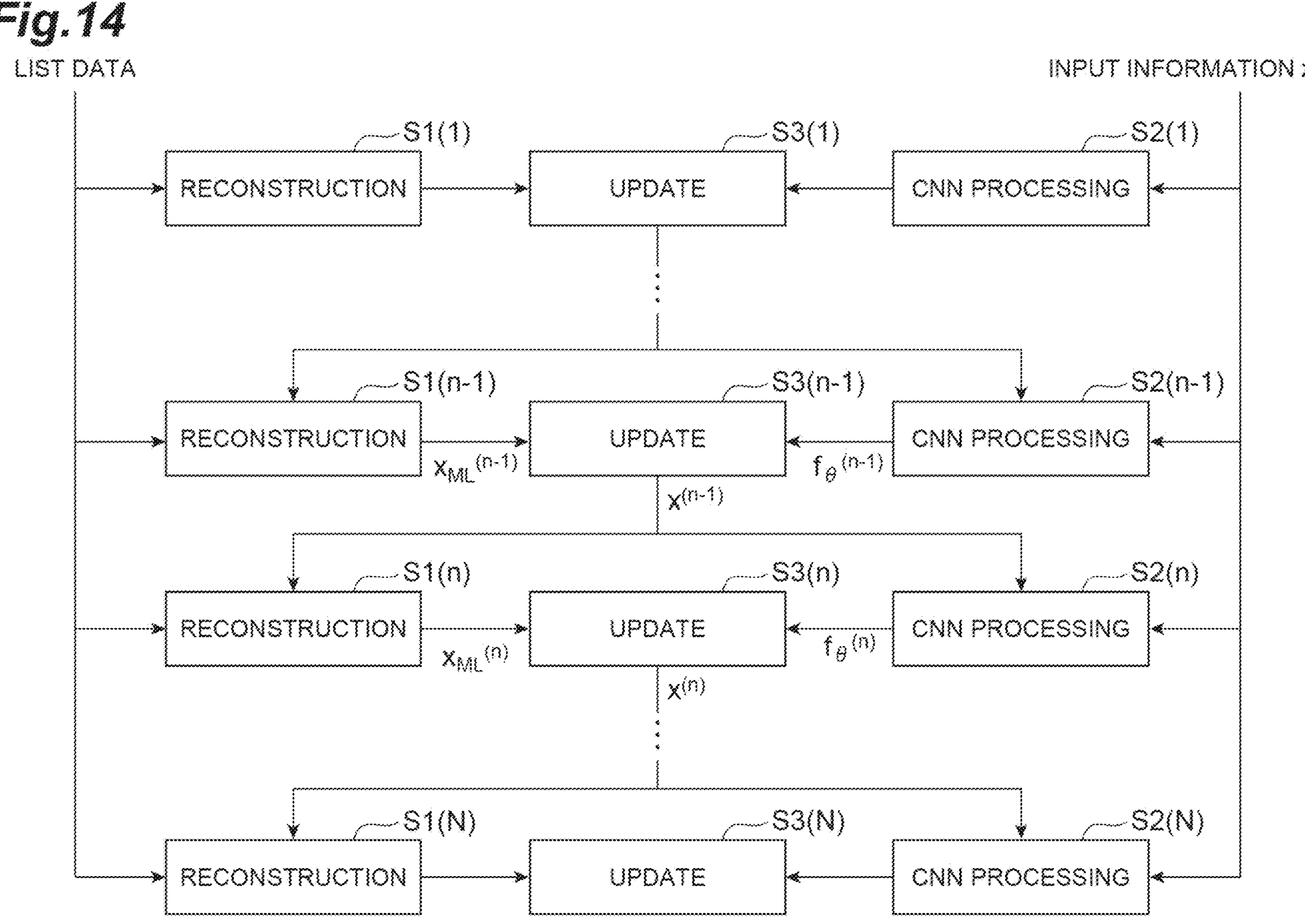
FIG. 14 is a diagram illustrating a sequence of the image processing method according to a second aspect.

FIG. 14 is a diagram illustrating a sequence of the image processing method according to the second aspect. Prior to performing the repeated processing, the training state $\theta^{(0)}$ of the CNN and the third image $x^{(0)}$ are respectively initialized.

In the n-th reconstruction step S1($n$), according to the above Formula (8), the first image $$x_{ML}^{(n)}$$

is created by performing the update of the third image $x^{(n-1)}$ based on the list data U by using the list mode iterative reconstruction method.

In the n-th CNN processing step S2($n$), according to the above Formula (9), the input information z is input to the CNN, and the second image $$f_\theta^{(n)}(z)$$

is created by the CNN, and further, the CNN is trained so as to bring the created second image $$f_\theta^{(n)}(z)$$

close to the third image $x^{(n-1)}$. The training state of the CNN after the above training is set to $\theta^{(n)}$.

In the n-th update step S3($n$), according to the above Formula (10) and Formula (11), the third image $x^{(n-1)}$ is updated to the third image $x^{(n)}$ based on the first image $$x_{ML}^{(n)}$$

and the second image $$f_\theta^{(n)}(z).$$

When the N times of the steps of the repeated processing of the reconstruction step S1, the CNN processing step S2, and the update step S3 are completed, any one of the first image $$x_{ML}^{(n)},$$

the second image $$f_\theta^{(N)}(z),$$

and the third image $x^{(N)}$ obtained as a result of the repeated processing is set as the tomographic image of the subject.

In the second aspect, the respective processes of the reconstruction step S1($n$) and the CNN processing step S2($n$) may be performed in any order, or may be performed in parallel.

The De Pierro method corresponds to a method in which it is set to $\rho=1$ and $\gamma=1/\omega$ in the FBS method. That is, in the De Pierro method, the following Formula (13) and Formula (14) are used in place of the above Formula (10) and Formula (11). The processing content of each of the reconstruction step S1, the CNN processing step S2, and the update step S3 is the same as described above.

[Formula 13]

$$x_{Reg}^{(n)} = x^{(n-1)} + \frac{1}{\omega}\left(f_{\theta^{(n)}}(z) - x^{(n-1)}\right) \tag{13}$$

[Formula 14]

$$x^{(n)} = \frac{2x_{ML}^{(n)}}{\left(1 - x_{Reg}^{(n)}\right) + \sqrt{\left(1 - x_{Reg}^{(n)}\right)^2 + 4x_{ML}^{(n)}}} \tag{14}$$

In the second aspect, the first image $X_{ML}$ and the second image $f_\theta(z)$ are not optimized at the same time, but the first image $X_{ML}$ and the second image $f_\theta(z)$ are optimized separately, and thus, it is easy to solve the problem. Further, the processing of the reconstruction step S1 performed by the reconstruction unit 11 and the processing of the CNN processing step S2 performed by the CNN processing unit 12 can be performed by the conventional techniques as described in, for example, Non Patent Documents 1 and 2, and thus, it is easy to implement.

As in the case of the first aspect, in the tomographic image obtained by the image processing method according to the second aspect also, the noise is reduced, and further, the structure of the cerebral cortex is well reconstructed. In the second aspect also, it is possible to generate a highly quantitative tomographic image while suppressing an increase in noise artifacts.

The present invention is not limited to the embodiments and configuration examples described above, and various modifications are possible. For example, the radiation tomography apparatus 2 is a PET apparatus in the above embodiment, and further, it may be a SPECT apparatus.

The image processing apparatus of the first aspect according to the above embodiment is an image processing apparatus for creating a tomographic image based on list data collected by a radiation tomography apparatus, and includes (1) a reconstruction unit for newly creating a first image by repeatedly performing processing of bringing an image obtained by updating the first image based on the list data by using a list mode iterative reconstruction method close to a difference between a second image and a third image; (2) a CNN processing unit for inputting input information to a convolutional neural network, creating the second image by the convolutional neural network, and training the convolutional neural network so as to bring the created second image close to a sum of the first image and the third image; and (3) an update unit for updating the third image based on the first image and the second image, and starting from an initial state of each of a training state of the convolutional neural network, the first image, the second image, and the third image, creation of the first image by the reconstruction unit, creation of the second image and training of the convolutional neural network by the CNN processing unit, and update of the third image by the update unit are repeatedly performed, and any one of the first image and the second image obtained by repeated processing is set as the tomographic image.

The image processing apparatus of the second aspect according to the above embodiment is an image processing apparatus for creating a tomographic image based on list data collected by a radiation tomography apparatus, and includes (1) a reconstruction unit for creating a first image by updating a third image based on the list data by using a list mode iterative reconstruction method; (2) a CNN processing unit for inputting input information to a convolutional neural network, creating a second image by the convolutional neural network, and training the convolutional neural network so as to bring the created second image close to the third image; and (3) an update unit for updating the third image based on the first image and the second image, and starting from an initial state of each of a training state of the convolutional neural network and the third image, creation of the first image by the reconstruction unit, creation of the second image and training of the convolutional neural network by the CNN processing unit, and update of the third image by the update unit are repeatedly performed, and any one of the first image, the second image, and the third image obtained by repeated processing is set as the tomographic image.

In the above image processing apparatus of the first or second aspect, the CNN processing unit may input an image representing form information of a subject to the convolutional neural network as the input information.

In the above image processing apparatus of the first or second aspect, the CNN processing unit may input an MRI image of a subject to the convolutional neural network as the input information. Further, the CNN processing unit may input a CT image of a subject to the convolutional neural network as the input information.

In the above image processing apparatus of the first or second aspect, the CNN processing unit may input a random noise image to the convolutional neural network as the input information.

The radiation tomography system according to the above embodiment includes a radiation tomography apparatus for collecting list data for reconstructing a tomographic image of a subject; and the image processing apparatus of the above configuration for creating the tomographic image based on the list data collected by the radiation tomography apparatus.

The image processing method of the first aspect according to the above embodiment is an image processing method for creating a tomographic image based on list data collected by a radiation tomography apparatus, and includes (1) a reconstruction step of newly creating a first image by repeatedly performing processing of bringing an image obtained by updating the first image based on the list data by using a list mode iterative reconstruction method close to a difference between a second image and a third image; (2) a CNN processing step of inputting input information to a convolutional neural network, creating the second image by the convolutional neural network, and training the convolutional neural network so as to bring the created second image close to a sum of the first image and the third image; and (3) an update step of updating the third image based on the first image and the second image, and starting from an initial state of each of a training state of the convolutional neural network, the first image, the second image, and the third image, creation of the first image in the reconstruction step, creation of the second image and training of the convolutional neural network in the CNN processing step, and update of the third image in the update step are repeatedly performed, and any one of the first image and the second image obtained by repeated processing is set as the tomographic image.

The image processing method of the second aspect according to the above embodiment is an image processing method for creating a tomographic image based on list data collected by a radiation tomography apparatus, and includes (1) a reconstruction step of creating a first image by updating a third image based on the list data by using a list mode iterative reconstruction method; (2) a CNN processing step of inputting input information to a convolutional neural network, creating a second image by the convolutional neural network, and training the convolutional neural network so as to bring the created second image close to the third image; and (3) an update step of updating the third image based on the first image and the second image, and starting from an initial state of each of a training state of the convolutional neural network and the third image, creation of the first image in the reconstruction step, creation of the second image and training of the convolutional neural network in the CNN processing step, and update of the third image in the update step are repeatedly performed, and any one of the first image, the second image, and the third image obtained by repeated processing is set as the tomographic image.

In the above image processing method of the first or second aspect, in the CNN processing step, an image representing form information of a subject may be input to the convolutional neural network as the input information.

In the above image processing method of the first or second aspect, in the CNN processing step, an MRI image of a subject may be input to the convolutional neural network as the input information. Further, in the CNN processing step, a CT image of a subject may be input to the convolutional neural network as the input information.

In the above image processing method of the first or second aspect, in the CNN processing step, a random noise image may be input to the convolutional neural network as the input information.

INDUSTRIAL APPLICABILITY

The present invention can be used as an image processing apparatus and an image processing method capable of creating a tomographic image in which noise is reduced based on list data collected by a radiation tomography apparatus.

REFERENCE SIGNS LIST

1—radiation tomography system, 2—radiation tomography apparatus, 10—image processing apparatus, 11—reconstruction unit, 12—CNN processing unit, 13—update unit, 14—storage unit.

The invention claimed is:

1. An image processing apparatus for creating a tomographic image based on list data collected by a radiation tomography apparatus, the image processing apparatus comprising:

a reconstruction unit configured to newly create a first image by repeatedly performing processing of bringing an image obtained by updating the first image based on the list data by using a list mode iterative reconstruction method close to a difference between a second image and a third image;

a CNN processing unit configured to input input information to a convolutional neural network, create the second image by the convolutional neural network, and train the convolutional neural network so as to bring the created second image close to a sum of the first image and the third image; and an update unit configured to update the third image based on the first image and the second image, wherein starting from an initial state of each of a training state of the convolutional neural network, the first image, the second image, and the third image, creation of the first image by the reconstruction unit, creation of the second image and training of the convolutional neural network by the CNN processing unit, and update of the third image by the update unit are repeatedly performed, and any one of the first image and the second image obtained by repeated processing is set as the tomographic image.

2. The image processing apparatus according to claim 1, wherein the CNN processing unit is configured to input an image representing form information of a subject to the convolutional neural network as the input information.

3. The image processing apparatus according to claim 1, wherein the CNN processing unit is configured to input an MRI image of a subject to the convolutional neural network as the input information.

4. The image processing apparatus according to claim 1, wherein the CNN processing unit is configured to input a CT image of a subject to the convolutional neural network as the input information.

5. The image processing apparatus according to claim 1, wherein the CNN processing unit is configured to input a random noise image to the convolutional neural network as the input information.

6. A radiation tomography system comprising:

a radiation tomography apparatus configured to collect list data for reconstructing a tomographic image of a subject; and the image processing apparatus according to claim 1 configured to create the tomographic image based on the list data collected by the radiation tomography apparatus.

7. An image processing apparatus for creating a tomographic image based on list data collected by a radiation tomography apparatus, the image processing apparatus comprising:

a reconstruction unit configured to create a first image by updating a third image based on the list data by using a list mode iterative reconstruction method;

a CNN processing unit configured to input input information to a convolutional neural network, create a second image by the convolutional neural network, and train the convolutional neural network so as to bring the created second image close to the third image; and an update unit configured to update the third image based on the first image and the second image, wherein starting from an initial state of each of a training state of the convolutional neural network and the third image, creation of the first image by the reconstruction unit, creation of the second image and training of the convolutional neural network by the CNN processing unit, and update of the third image by the update unit are repeatedly performed, and any one of the first image, the second image, and the third image obtained by repeated processing is set as the tomographic image.

8. The image processing apparatus according to claim 7, wherein the CNN processing unit is configured to input an image representing form information of a subject to the convolutional neural network as the input information.

9. The image processing apparatus according to claim 7, wherein the CNN processing unit is configured to input an MRI image of a subject to the convolutional neural network as the input information.

10. The image processing apparatus according to claim 7, wherein the CNN processing unit is configured to input a CT image of a subject to the convolutional neural network as the input information.

11. The image processing apparatus according to claim 7, wherein the CNN processing unit is configured to input a random noise image to the convolutional neural network as the input information.

12. A radiation tomography system comprising:

a radiation tomography apparatus configured to collect list data for reconstructing a tomographic image of a subject; and the image processing apparatus according to claim 2 configured to create the tomographic image based on the list data collected by the radiation tomography apparatus.

13. An image processing method for creating a tomographic image based on list data collected by a radiation tomography apparatus, the image processing method comprising:

a reconstruction step of newly creating a first image by repeatedly performing processing of bringing an image obtained by updating the first image based on the list data by using a list mode iterative reconstruction method close to a difference between a second image and a third image;

a CNN processing step of inputting input information to a convolutional neural network, creating the second image by the convolutional neural network, and training the convolutional neural network so as to bring the created second image close to a sum of the first image and the third image; and an update step of updating the third image based on the first image and the second image, wherein starting from an initial state of each of a training state of the convolutional neural network, the first image, the second image, and the third image, creation of the first image in the reconstruction step, creation of the second image and training of the convolutional neural network in the CNN processing step, and update of the third image in the update step are repeatedly performed, and any one of the first image and the second image obtained by repeated processing is set as the tomographic image.

14. The image processing method according to claim 13, wherein in the CNN processing step, an image representing form information of a subject is input to the convolutional neural network as the input information.

15. The image processing method according to claim 13, wherein in the CNN processing step, an MRI image of a subject is input to the convolutional neural network as the input information.

16. The image processing method according to claim 13, wherein in the CNN processing step, a CT image of a subject is input to the convolutional neural network as the input information.

17. The image processing method according to claim 13, wherein in the CNN processing step, a random noise image is input to the convolutional neural network as the input information.

18. An image processing method for creating a tomographic image based on list data collected by a radiation tomography apparatus, the image processing method comprising:

a reconstruction step of creating a first image by updating a third image based on the list data by using a list mode iterative reconstruction method;

a CNN processing step of inputting input information to a convolutional neural network, creating a second image by the convolutional neural network, and training the convolutional neural network so as to bring the created second image close to the third image; and an update step of updating the third image based on the first image and the second image, wherein starting from an initial state of each of a training state of the convolutional neural network and the third image, creation of the first image in the reconstruction step, creation of the second image and training of the convolutional neural network in the CNN processing step, and update of the third image in the update step are repeatedly performed, and any one of the first image, the second image, and the third image obtained by repeated processing is set as the tomographic image.

19. The image processing method according to claim 18, wherein in the CNN processing step, an image representing form information of a subject is input to the convolutional neural network as the input information.

20. The image processing method according to claim 18, wherein in the CNN processing step, an MRI image of a subject is input to the convolutional neural network as the input information.

21. The image processing method according to claim 18, wherein in the CNN processing step, a CT image of a subject is input to the convolutional neural network as the input information.

22. The image processing method according to claim 18, wherein in the CNN processing step, a random noise image is input to the convolutional neural network as the input information.

* * * * *